United States Patent [19]
Seeber

[11] Patent Number: 5,685,474
[45] Date of Patent: Nov. 11, 1997

[54] TACTILE INDICATOR FOR SURGICAL INSTRUMENT

[75] Inventor: Lynn M. Seeber, Stoughton, Mass.

[73] Assignee: United States Surgical Corporation, Norwalk, Conn.

[21] Appl. No.: 324,186

[22] Filed: Oct. 4, 1994

[51] Int. Cl.[6] ............... A61B 17/068; A61B 17/115
[52] U.S. Cl. ............. 227/179.1; 227/19; 227/175.1
[58] Field of Search ................... 227/175.1, 176.1, 227/177.1, 178.1, 179.1, 180.1, 181.1, 182.1, 19

[56] References Cited

U.S. PATENT DOCUMENTS

| | | | |
|---|---|---|---|
| 4,202,480 | 5/1980 | Annett | 227/19 X |
| 4,289,133 | 9/1981 | Rothfuss | 227/19 X |
| 4,319,576 | 3/1982 | Rothfuss | 227/19 X |
| 4,379,457 | 4/1983 | Gravener et al. | 227/156 X |
| 4,506,670 | 3/1985 | Crossley | 227/181.1 |
| 4,527,724 | 7/1985 | Chow et al. | 227/19 X |
| 5,005,749 | 4/1991 | Aranyi | 227/19 |
| 5,129,570 | 7/1992 | Schulze et al. | 227/19 |
| 5,137,198 | 8/1992 | Nobis et al. | 227/19 |
| 5,193,731 | 3/1993 | Aranyi | 227/19 |
| 5,275,323 | 1/1994 | Schulze et al. | 227/176.1 |
| 5,356,064 | 10/1994 | Green et al. | 227/177.1 |
| 5,364,002 | 11/1994 | Green et al. | 227/177.1 |
| 5,464,144 | 11/1995 | Guy et al. | 227/176.1 |
| 5,497,933 | 3/1996 | DeFonzo et al. | 227/175.1 |
| 5,497,934 | 3/1996 | Brady et al. | 227/176.1 |
| 5,503,320 | 4/1996 | Webster et al. | 227/176.1 |

*Primary Examiner*—Joseph J. Hail, III
*Assistant Examiner*—Jay A. Stelacone

[57] ABSTRACT

A surgical instrument having a tactile and audible firing indicator is disclosed. The instrument has preferred features which include a tactile and audible indicator disposed in the handle housing for indicating to a user when the instrument has been properly and completely actuated.

20 Claims, 9 Drawing Sheets

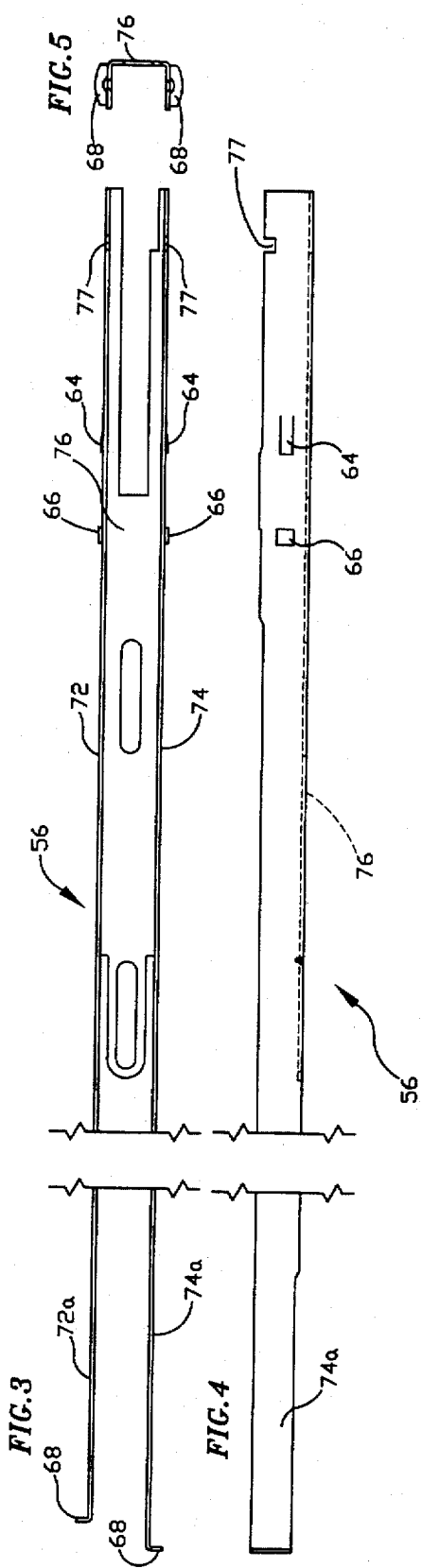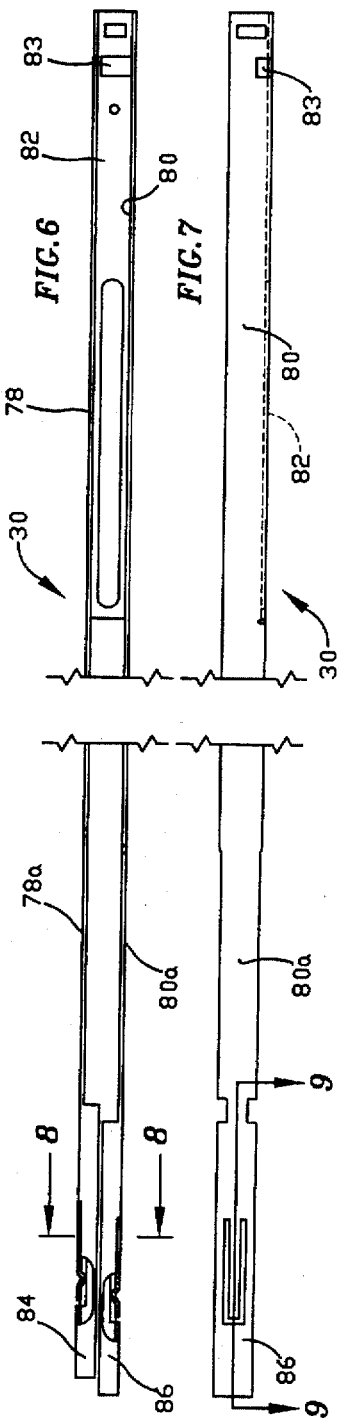

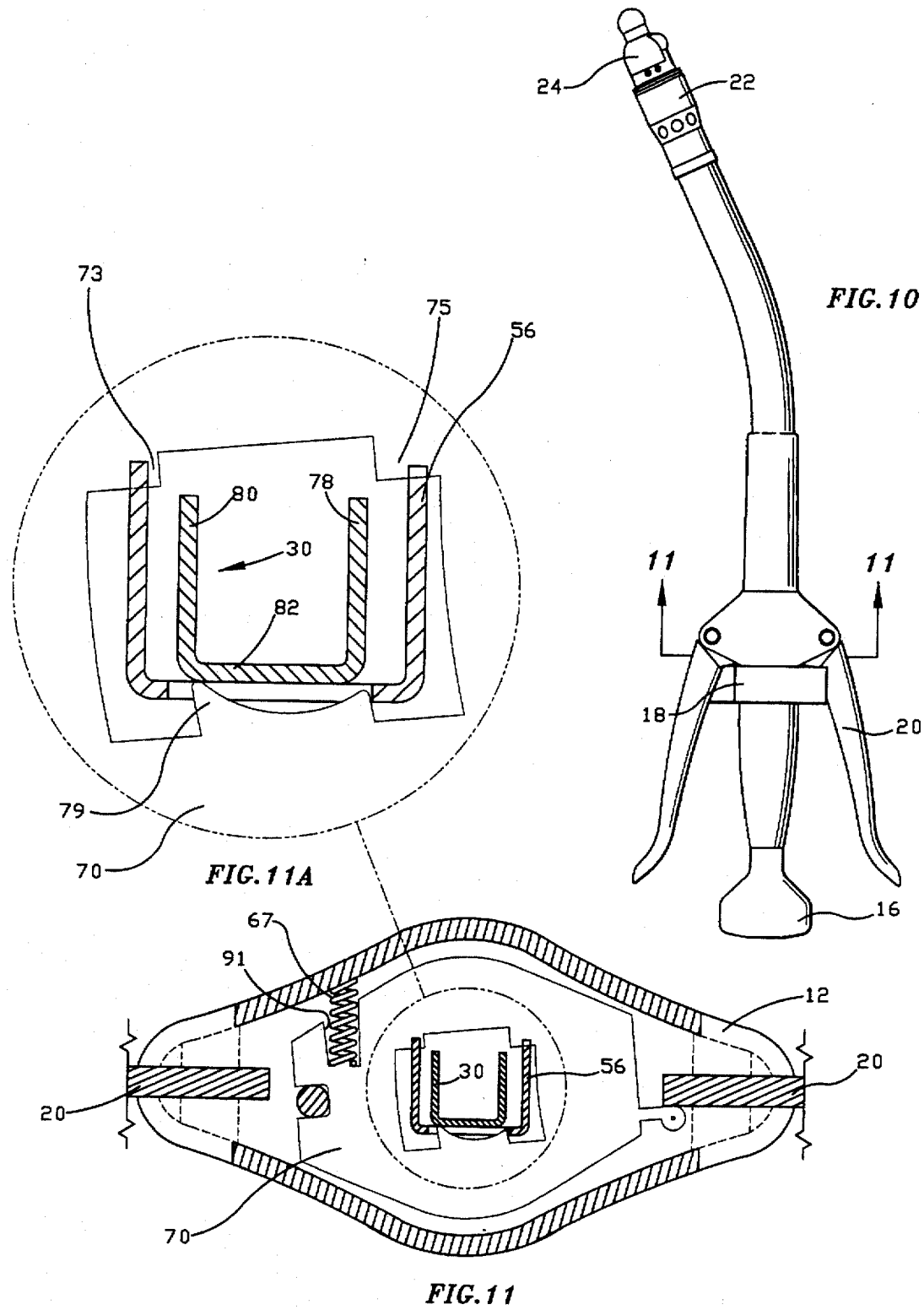

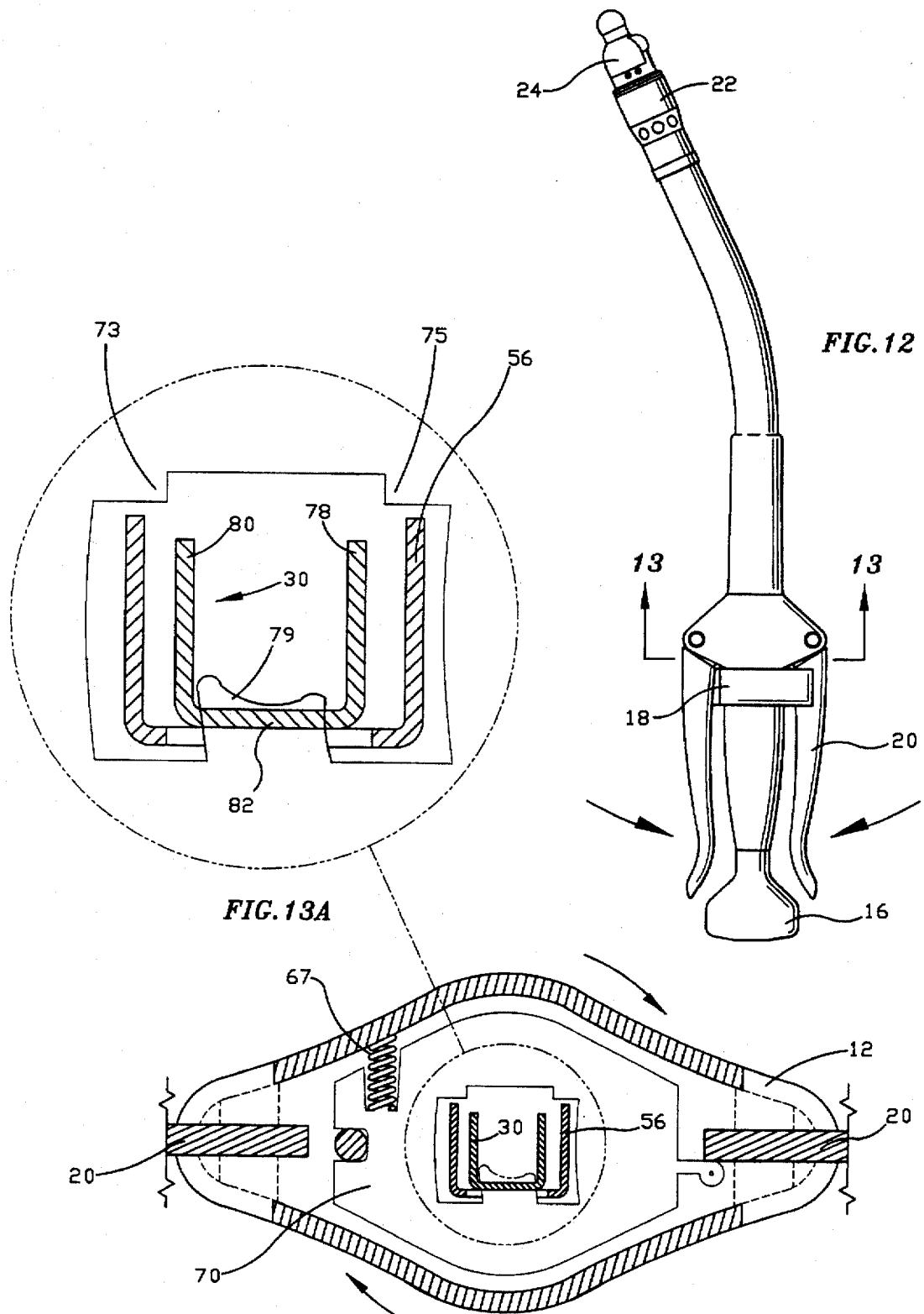

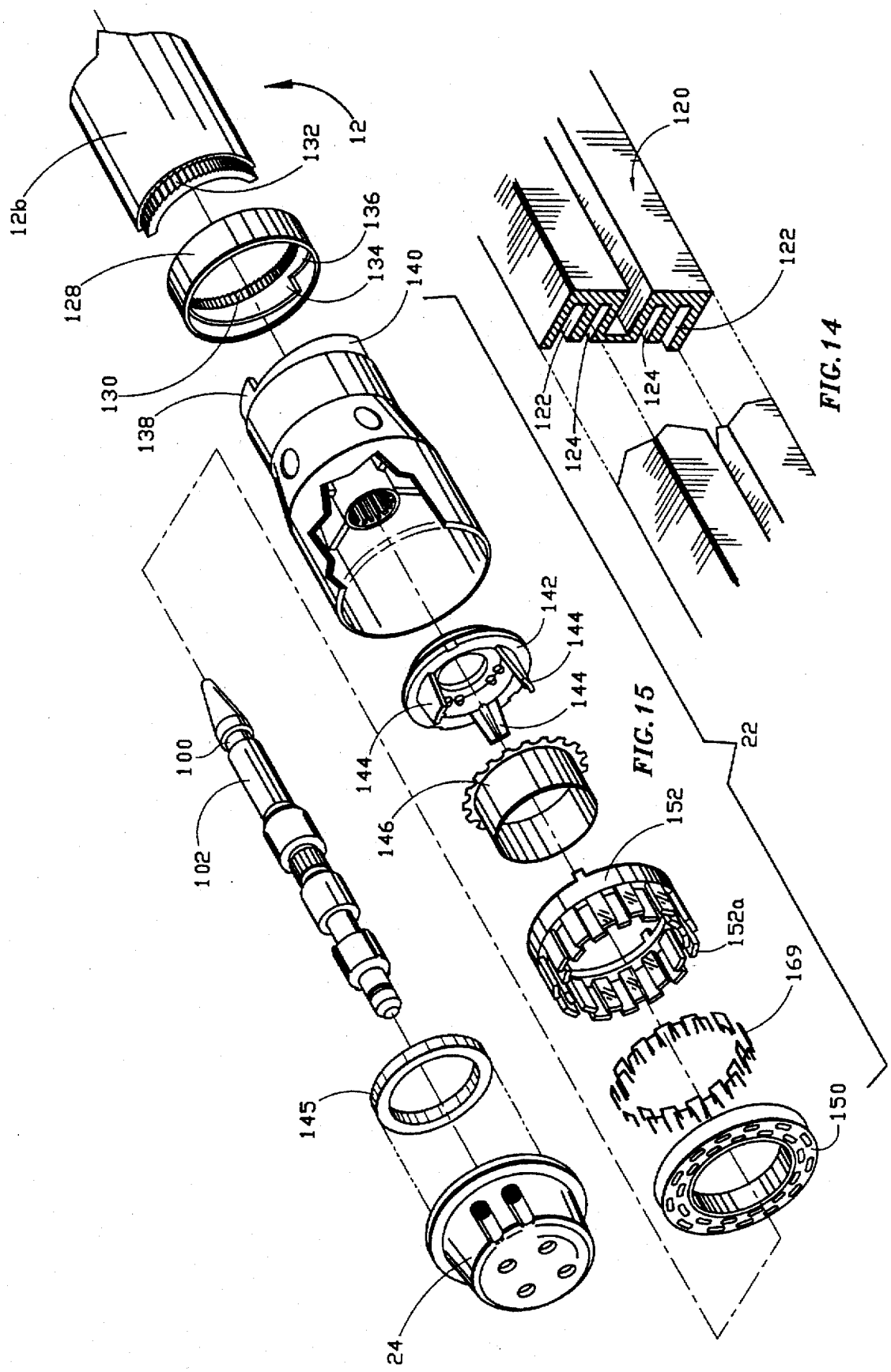

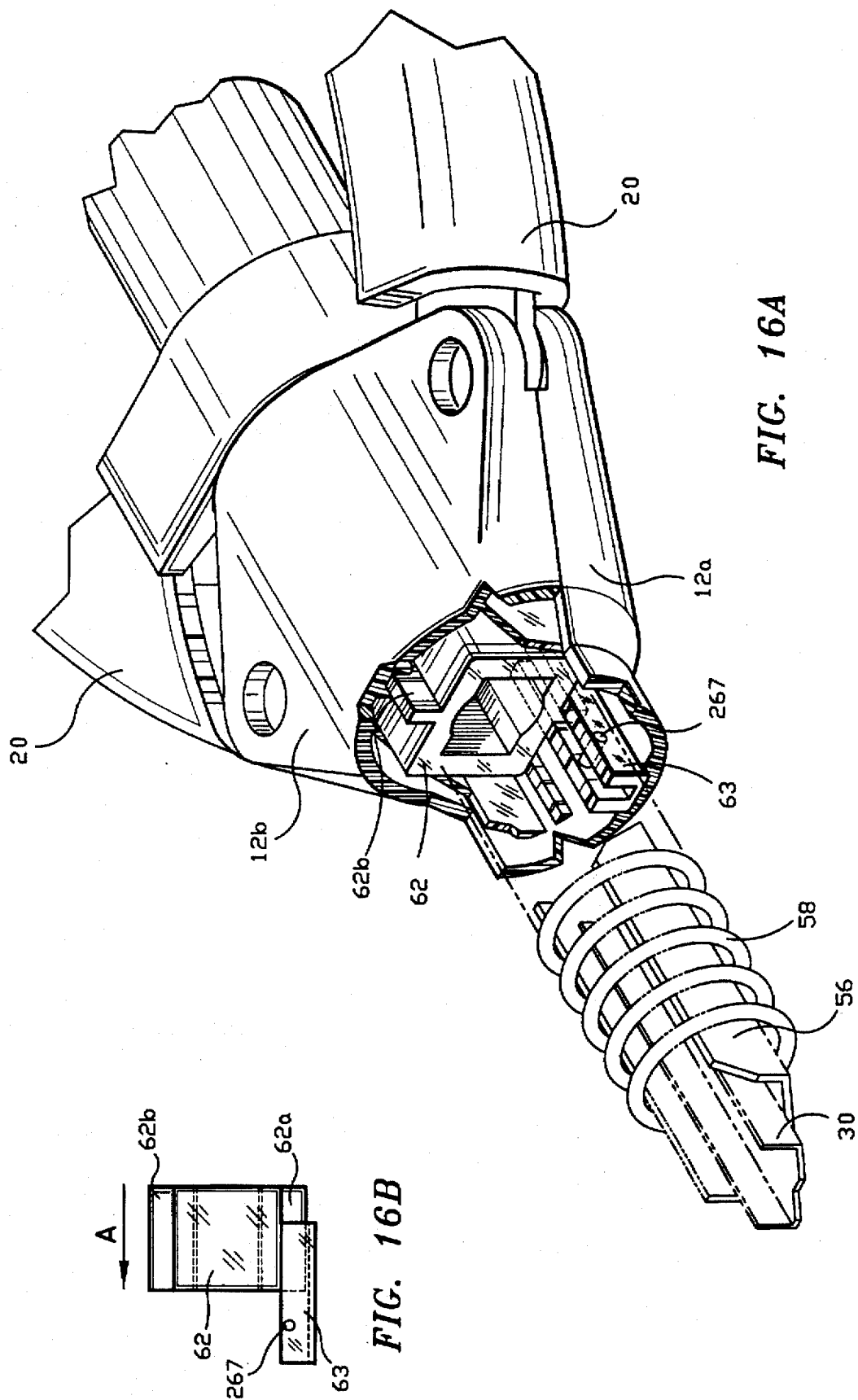

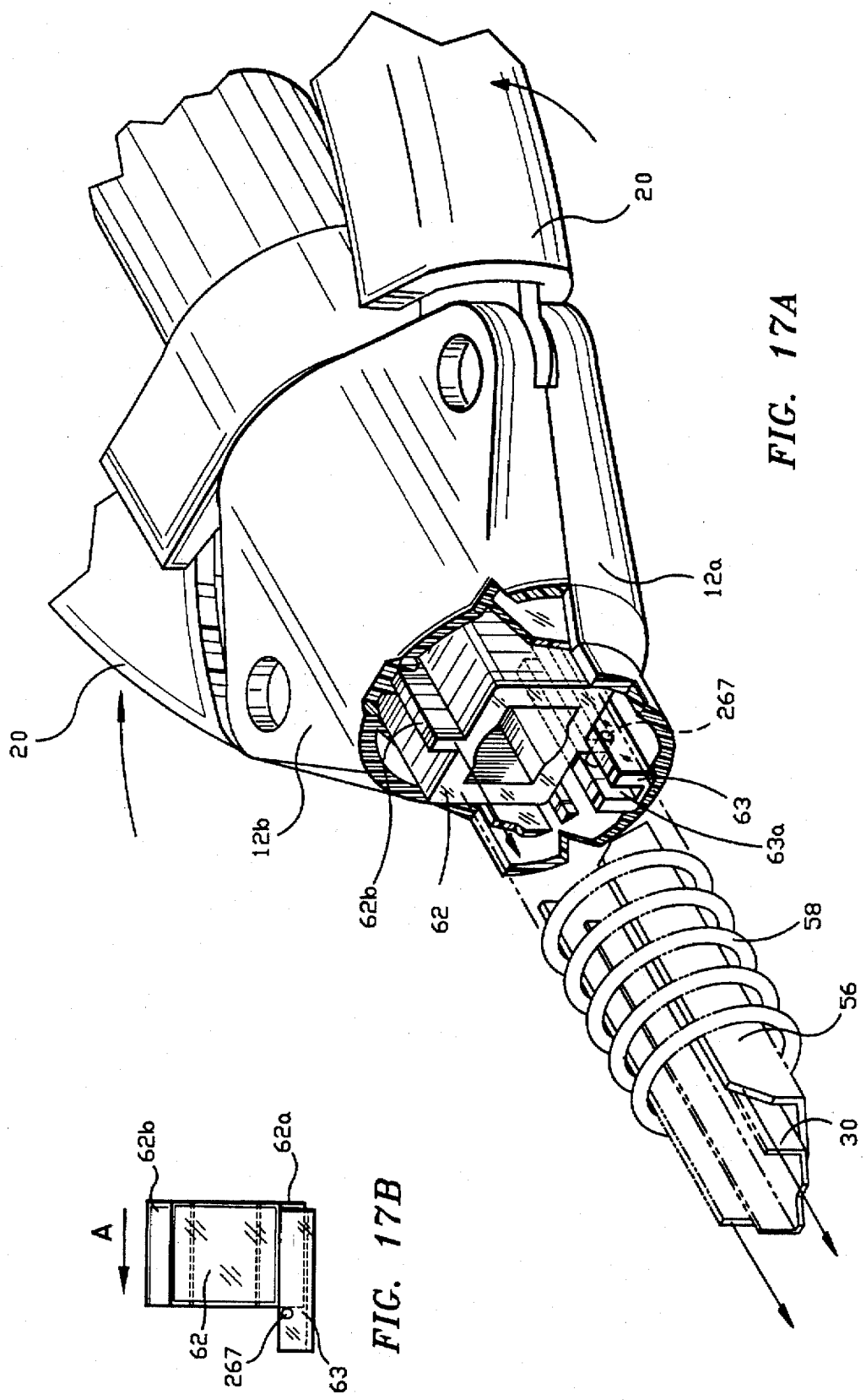

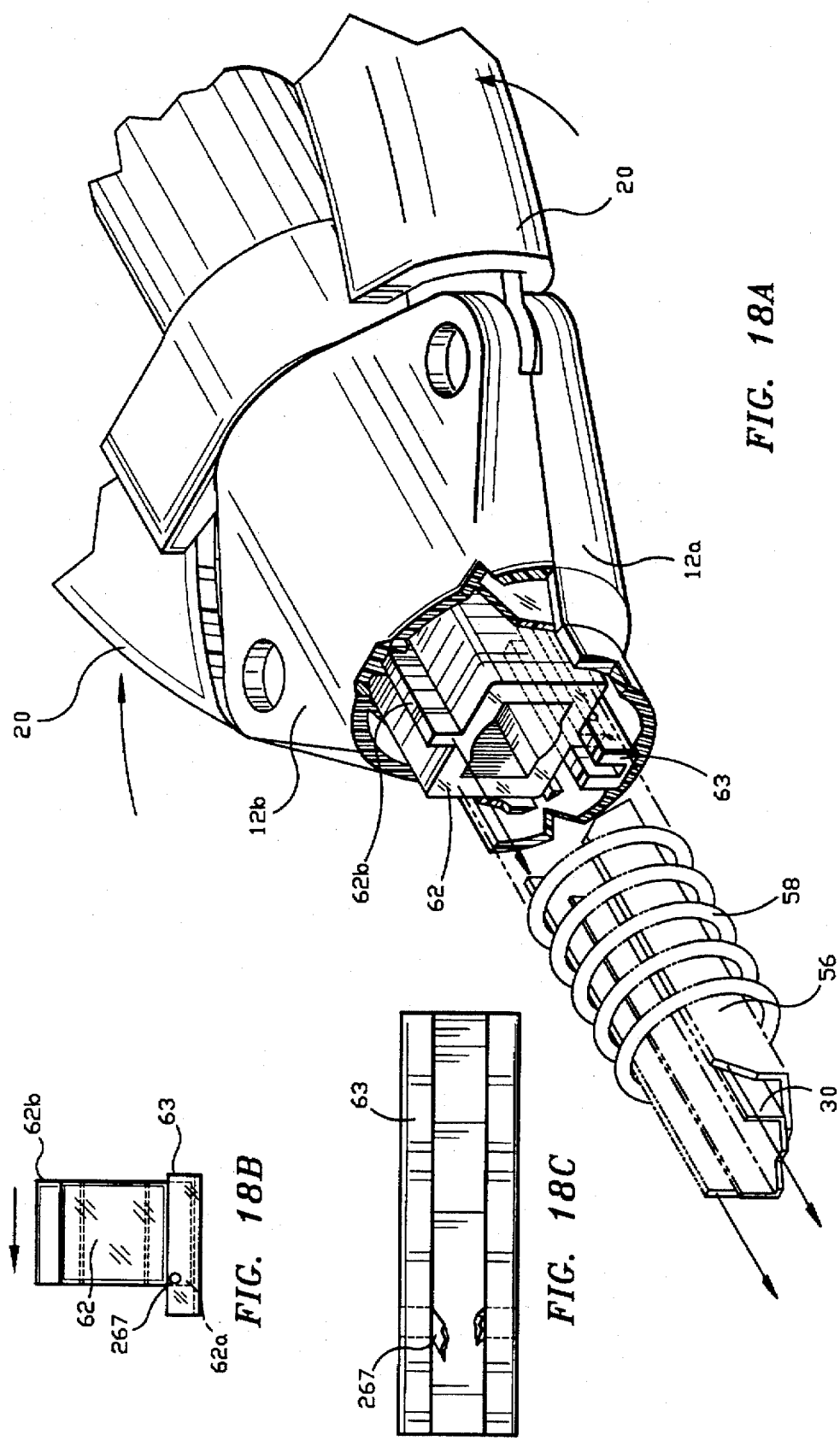

TACTILE INDICATOR FOR SURGICAL INSTRUMENT

BACKGROUND

1. Field of the Invention

The present disclosure relates to surgical instruments. More particularly, this disclosure relates to surgical instruments having an audible and tactile indicator for determining that the instrument has been actuated.

2. Description of the Related Art

Various types of surgical fastener applying instruments have been known for the application of surgical fasteners to tissue. For example, it has been known to use various types of surgical staplers in gastric and esophageal surgery in both classic or modified gastric reconstructions performed end-to-end, end-to-side or side-to-side. In many cases, instruments, such as described in U.S. Pat. No. 4,603,693, have been used where an anvil assembly mounted on the end of a center rod can be manipulated relative to a staple assembly on the end of a tubular housing of the instrument. In instruments of this nature, the center rod is connected with a mechanism, for example, which employs a wing nut at the proximal end of the instrument, so that the rod can be moved back and forth independently of the staple assembly so as to adjust the anvil assembly relative to the staple assembly. Likewise, a pusher tube is mounted within the instrument for movement via a handle mechanism so as to cause a firing of the staples from the staple assembly towards the anvil assembly.

In some instruments, such as described in U.S. Pat. No. 4,351,466, these stapling instruments have been provided with a pair of handles in order to actuate the pusher tube to cause a firing of the staples. In such cases, each handle has been pivotally mounted so as to be moved toward the other handle during manual squeezing by a surgeon. Each handle also includes a lever arm within the instrument which engages against the pusher tube so as to move the tube in a distal direction. In most surgical stapling applications, proper staple formation is very important to achieve the desired anastomosis. As such, proper alignment of parts during manufacture and precise mechanisms to control staple formation during use are advantageous.

During minimally invasive surgical procedures where it is sometimes difficult to ascertain precisely, the relative position or firing state of instruments used during such procedures. Indicators have been developed to assist surgeons in identifying when, for example, the staples of a surgical stapling instrument have been completely formed. Examples of such indicators can be found in U.S. Pat. Nos. 4,289,133 to Rothfuss, 4,379,457 to Gravener et al., and 5,193,731 to Aranyi. These devices employ either a visual indicator in the handle or a frangible member disposed in the stapling head of the instrument.

It is desirable to have an improved indicator providing both tactile and audible indication to the user when the desired state of the instrument has been completely reached, for example, the formation of surgical staples or other fasteners.

SUMMARY

The present disclosure provides an audible and tactile indication mechanism for surgical instruments which indicates to the user when the instrument has been completely actuated.

A surgical instrument is provided which includes a housing having a proximal end portion and a distal end portion; an elongated shaft extending from the housing; a tool mechanism operatively positioned at the elongated shaft distal end portion and operable between a first position and a second position; an actuation mechanism operable between a first position and a second position to provide corresponding movement of the tool mechanism between the first and second positions, respectively, thereof; and an indicator mechanism including a frangible member which provides audible and tactile indication upon substantially complete movement of the actuation mechanism from the first position to the second position, thereof. The frangible member is preferably a pin formed of a metallic material, such as aluminum, and is preferably removably mounted in the housing.

In a preferred embodiment, the actuator mechanism includes a block member which is slidably mounted within the housing and has an extended portion formed thereon which is configured and dimensioned to slide within a guide member longitudinal slot. The frangible member is positioned within the slot such that the frangible member is broken upon distal movement of the block by a predetermined distance.

In a particular preferred embodiment, the present disclosure provides a surgical instrument for applying at least one circular array of fasteners which includes a housing; an elongated shaft extending from the housing; a fastener carrying cartridge operatively positioned at the elongated shaft distal end portion; an anvil member operatively disposed adjacent the fastener carrying cartridge; an actuation mechanism disposed on the housing and operatively associated with the fastener carrying cartridge to deploy surgical fasteners therefrom; and an indicator mechanism including a frangible member operatively associated with the actuation mechanism, which provides audible and tactile indication upon actuation of the surgical instrument.

BRIEF DESCRIPTION OF THE DRAWINGS

Preferred embodiments of a surgical stapling instrument are described hereinbelow with reference to the drawings wherein:

FIG. 3 is a top plan view of the fastener firing member of the present disclosure;

FIG. 4 is a side plan view of the fastener firing member of FIG. 3;

FIG. 5 is an end view of the fastener firing member of FIG. 3;

FIG. 6 is a top plan view of the elongated member for moving the anvil of the instrument described in present disclosure relative to the stapling cartridge thereof;

FIG. 7 is a side plan view of the elongated member of FIG. 6;

FIG. 8 is a cross-sectional view taken along section line 8—8 of FIG. 6;

FIG. 9 is a cross-sectional view taken along section line 9—9 of FIG. 7;

FIG. 10 is a plan view of the instrument showing the lever members in the unfired position;

FIG. 11 is a cross-sectional view taken along section line 11—11 of FIG. 10;

FIG. 11A is an enlarged view of the area indicated in FIG. 11;

FIG. 12 is a plan view of the instrument showing the lever members in the fired position;

FIG. 13 is a cross-sectional view taken along section line 13—13 of FIG. 12;

FIG. 13A is an enlarged view of the area indicated on FIG. 13;

FIG. 14 is an enlarged, partially cut away crosssection view of the insert guide of the instrument of FIGS. 1 and 2;

FIG. 15 is an enlarged exploded view of the distal end of the instrument of FIG. 14;

FIG. 16A is an enlarged partially cut-away view of the handle section showing the pusher block and indicator components of the present disclosure;

FIG. 16B is an isolated elevation view of the components of the indicator of the present disclosure;

FIGS. 17A-18B are progressive views of the firing of the instrument and relative positioning of the components of the indicator of the present disclosure;

FIG. 18C is a top plan view of the pin of the tactile indicator after firing of the instrument.

DETAILED DESCRIPTION OF THE PREFERRED EMBODIMENTS

Figure 1:
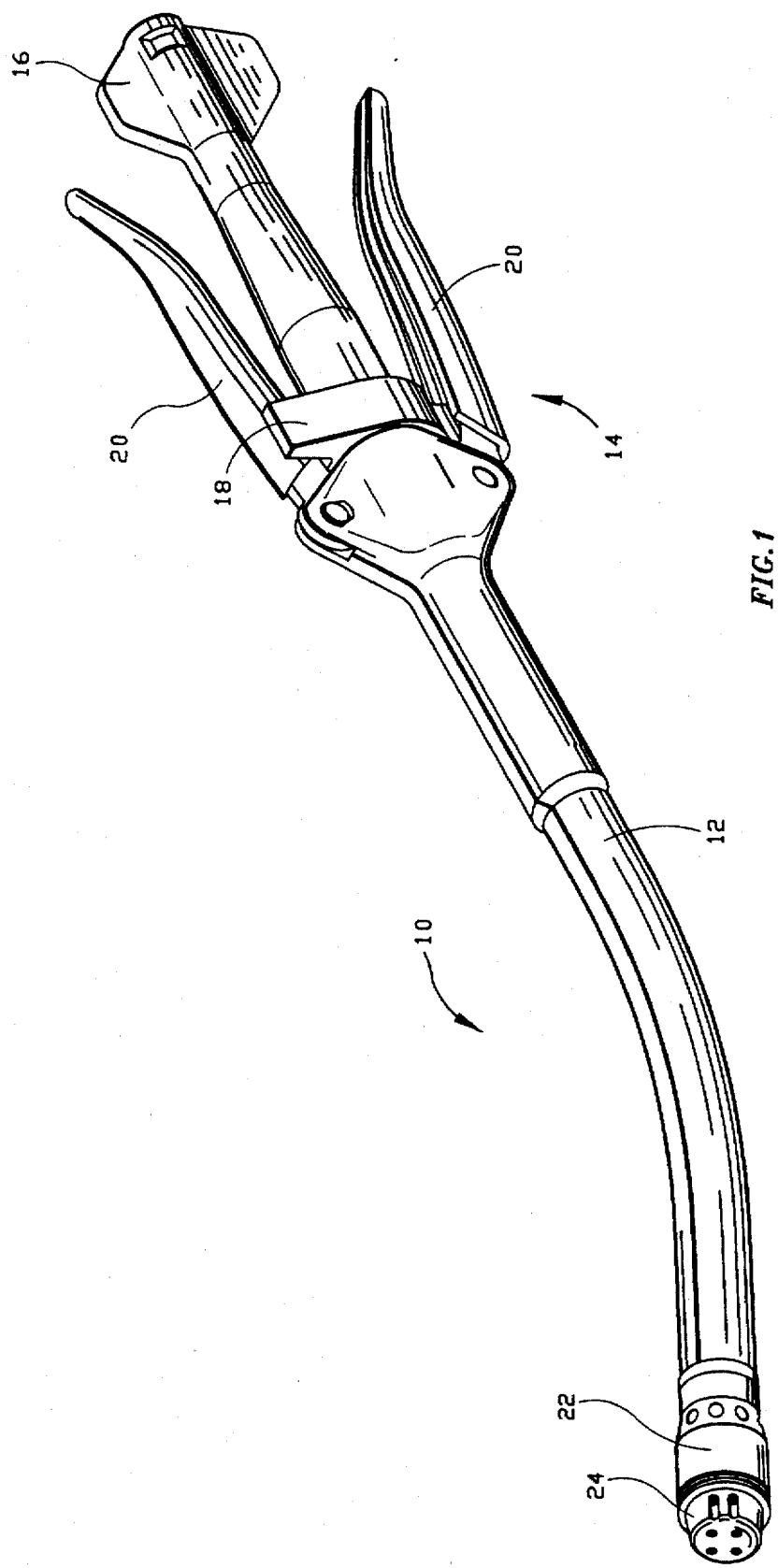
FIG. 1 is a perspective view of a surgical stapling instrument constructed according to the present disclosure for applying surgical fasteners to tissue.

Referring now in specific detail to the drawings, in which like reference numerals identify similar or identical elements throughout the several views, and initially to FIG. 1, which shows a preferred embodiment of the surgical instrument for applying a circular array of fasteners of the present disclosure illustrated in perspective view as instrument 10. Instrument 10 includes elongate body portion 12 and handle section 14. Handle section 14 includes anvil adjustment member 16, lever lockout or safety member 18 and fastener firing levers 20. Fastener head portion 22 and anvil member 24 are disposed at the distal end of body portion 12.

Except where noted otherwise, the materials utilized in the components of the surgical instrument of the present disclosure generally include such materials as polycarbonate for housing sections and related components, and stainless steel for such components which transmit forces. One preferred polycarbonate material is LEXAN® brand polycarbonate available from General Electric Company. However, equivalent alternative materials will readily come to the mind of those skilled in the art.

Figure 2:
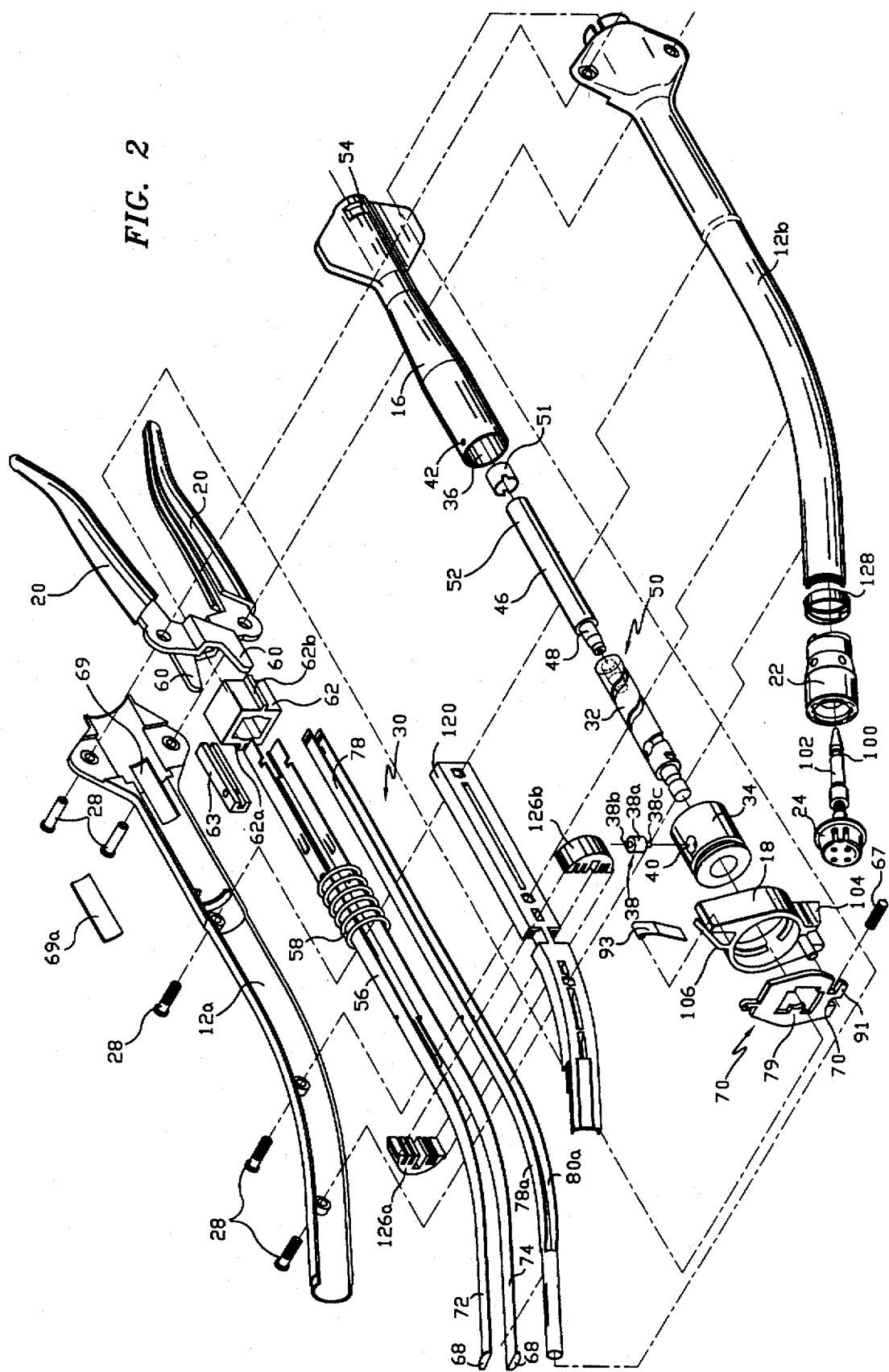
FIG. 2 is an exploded perspective view of an instrument in accordance with the present disclosure.

Referring now to FIG. 2, the various components of instrument 10 are shown in exploded view. Instrument 10 includes body or housing half sections 12a and 12b which are preferably molded and joined together by suitable fastening means such as rivets 28, or the like. To control axial movement of anvil member 24, elongated member 30 is slidably mounted within body portion 12, preferably by being securely mounted to helical cam member 32 by any suitable means such as, for example, welding or the like. Helical cam member 32 is slidably mounted within anvil adjustment member 16 by way of bushing 34 which is securely mounted in open end 36 of anvil adjustment member 16. Friction member 93 is disposed adjacent anvil adjustment member 16 to prevent relatively free rotation of the anvil adjustment member.

In a preferred embodiment, both the mounting of bushing 34 and the camming of helical cam 32 are accomplished by compound pin 38 which has central portion 38a and extending portions 38b and 38c which are of reduced diameter. Portions 38a and 38b are press fitted into bores 40 and respectively, located on bushing 34 and anvil adjustment member 16, respectively. Lower extending portion 38c serves as a camming pin and fits within the helical groove formed on the surface of helical cam 32. Anvil approximation indicator member 46 has extended portion 48 and is press fitted into proximal portion 50 of helical cam 32. Cap 51 is attached to proximal end 52 of anvil approximation indicator member 46. Cap 51 is preferably a colored piece which is easily visible through opening 54 formed near the proximal end of anvil adjustment member 16 to provide indication to the user when the anvil member is in the proper position for firing of the instrument. The distal end of elongated member 30 is provided with means to retain anvil member 24, which will be described in more detail below.

The fastener firing mechanism of instrument 10 includes elongated fastener firing member 56 which may be in the form of a u-shaped stainless steel member which is slidably mounted within body portion 12 preferably such that fastener firing member 56 is disposed around elongated member 30. Fastener firing member 56 is preferably biased in a proximal direction by suitable biasing means such as spring 58. Fastener firing levers 20 are pivotably mounted to body portion 12 and have extended portions 60 which cross over each other in scissor-like fashion. Pusher block 62 is mounted on fastener firing member 56, for example, being held between flexible finger portions 64 and raised portions 66 which are formed in the side walls of fastener firing member 56, as best illustrated in FIGS. 3 and 4. Fastener firing member 56 has bearing surfaces such as tabs 68 formed at the distal portion which serve to urge a pusher member 152 (FIG. 15) within fastener head portion 22 in a distal direction in order to eject surgical fasteners, such as stainless steel or titanium staples, from a fastener cartridge such as staple cartridge 150 disposed in the distal end of fastener head portion 22.

Referring again to FIG. 2, pusher block 62 is provided with extended key portions 62a and 62b which interact with an indicator mechanism to provide indication to the user upon complete formation of surgical staples 169 (FIG. 15). The indication mechanism preferably includes a keyway in which extended portion 62a is guided. To allow for testing of the instrument, the indicator mechanism is preferably a slotted guide member such as guide 63 which is removable from the housing of instrument 10 through opening 69 formed in housing half section 12a. Cover 69a is placed securely in opening 69 and can be either permanently bonded in place or can be removably attached to provide for easy access to the indicator mechanism. Guide 63 has frangible pin 267 mounted transverse to longitudinal slot 63a formed along a surface of the guide (as best seen in FIGS. 16A-18C). Pin 267 is preferably press fit into throughbores formed in the side walls of guide 63 which form longitudinal slot 63a. In a preferred embodiment, the pin is made from aluminum of a diameter between 0.10-0.080 inch and most preferably 038 inch.

Also disposed on instrument 10 are two lockout devices, lockout member 18 formed to lockout firing levers 20 and lockout member 70 formed to lockout movement of elongated member 30 which controls approximation of anvil 24 and fastener firing member 56. Lockout member 18 is preferably spring biased to the locked out position by spring 67 in slot 91 (as best shown in FIG. 11). Each of these lockout members are preferably mounted on instrument 10 in such a manner that they are fixed relative to each other and upon pivoting of lockout member 18, lockout member 70 also pivots. With reference to FIGS. 11A and 13A, lockout member 70 has shoulder portions 73 and 75 formed therein as well as inwardly extending tab 79. The function of each of these portions of lockout member 70 will be described in further detail below.

Referring now to FIGS. 3–9, the structural and functional details of fastener firing member 56 and elongated member 30 will now be described in detail. In FIGS. 3–5, fastener firing member 56 is shown as preferably being a generally U-shaped member formed from material which can transmit forces effectively and reliably such as stainless steel. Fastener firing member 56 has side walls 72 and 74 which are connected by web 76. To fit fastener firing member 56 within the curved section of body portion 12 (FIG. 1), fastener firing member 56 has extended portions or flexible bands 72a and 74a which are preferably formed as extensions of walls 72 and 74, respectively. Band 72a is shorter than band 74a. The difference in the length of the two bands corresponds to the amount of curvature of body portion 12 so that when fastener firing member 56 is mounted in body portion 12, the surfaces of tabs 68 form a plane parallel with the surface of the fastener pusher member (FIG. 2).

Referring to FIGS. 6–9, elongated member 30 is shown as a U-shaped member, similar to fastener firing member 56. Elongated member 30 has side walls 78 and 80 which are joined by web portion 82. However, the cross-section dimensions of elongated member 30 are preferably such that elongated member 30 readily fits within fastener firing member 56. This arrangement is desirable so that elongated member 30 and fastener firing member 56 can slide independent of each other. As with fastener firing member 56, elongated member 30 must also be formed to fit within the curved contour of body portion 12. To accomplish this curvature, elongated member 30 has extended portions or flexible bands 78a and 80a which are preferably formed integrally with walls 78 and 80, respectively. Similar to the construction of fastener firing member 56, bands 78a and 80a of elongated member 30 are of different length. Elongated member 30 terminates at a distal end in a pair of opposed anvil retaining portions 84 and 86. Preferably, structure can be provided within body portion 12 (see 120 in FIGS. 2 and 14) that serves to retain the side walls and bands of both elongated member 30 and fastener firing member 56. Such structure can be of unitary construction and have grooves to direct longitudinal movement of the channels and bands. Additionally, one or more seals (see 126a and 126b in FIG. 2) can be disposed within body portion 12 to prevent the flow of gases therethrough.

To facilitate retaining anvil member 24, and in particular, the anvil shaft therein, anvil retaining portions 84 and 86 are preferably semi-circular in shape as best illustrated in the cross-section view of FIG. 8. To assist in retention of anvil 24, anvil retaining portions 84 and 86 are provided with flexible finger portions 88 and 90, respectively, each of which have a raised portion formed thereon, such as camming and retaining portions 92 and 94, respectively. Camming surfaces 96 and 98 formed by camming and retaining portions 92 and 94, respectively serve to cam flexible finger portions 88 and 90 radially outward upon insertion of the anvil into the distal end of instrument 10. Once annular groove portion 100 (FIG. 15) of anvil shaft 102 passes between retaining portions 84 and 86, flexible finger portions 88 and 90 return toward their initial or at rest state so that retaining portions 92 and 94 seat in annular groove 100.

In a preferred embodiment, extended portions 78a and 80a of elongated member 30 are preferably bent until the ends of anvil retaining portions 84 and 86 are aligned and are then permanently joined together (as shown in FIG. 2), by suitable bonding techniques, such as by welding.

At the proximal end of elongated member 30, cut-out portion 83 is formed to receive lockout member 70 when elongated member 30 and, therefore, anvil 24 are properly positioned for firing the staples 169 (FIG. 15) of instrument 10. As best illustrated in FIGS. 6 and 7, cut-out portion 83 is preferably formed through most of web 82 and continues partially up side wall 80.

An insert guide 120 (FIG. 2) is provided and is preferably molded to conform to the curvature of housing half sections 12a and 12b so as to provide structural support for elongated member 30 and fastener firing member 56. In FIG. 14, insert guide 120 is illustrated in a partially cut away section to show the guide tracks which receive elongated member 30 and fastener firing member 56 therein. Specifically, outer guide tracks 122 are molded to receive sidewalls 72 and 74 therein and inner guide tracks 124 are formed to receive side walls 78 and 80 of elongate member 30 therein. Insert guide 120 thereby provides structural support upon longitudinal motion of either elongated member 30 or fastener firing member 56, particularly at the point of curvature thereof. Insert guide 120 effectively reduces possible force transmission losses upon operation of instrument 10.

In order to provide an internal seal in body portion 12, seal half sections 126a and 126b are formed to fit around notches formed on insert guide 120. Seal half sections 126a and 126b are preferably molded of a hard rubber material which is molded to conform with the inner dimensions of housing half sections 12a and 12b. Additionally, seal half sections 126a and 126b are molded to fit over elongated member 30 and fastener firing member 56 so as to form a seal between the internal section of the instrument 10 which is distal of the seal half sections 126a and 126b and the internal portions of instrument 10 which are proximal of seal half sections 126a and 126b so as to inhibit the passage of gases thereby.

In FIG. 15, an adjusting member such as collar 128 is mounted between the distal end of housing 12 and the proximal end of fastener head portion assembly 22. Collar 128 may include, for example, ratchet teeth 130 formed on an inner surface thereof at the proximal end. Ratchet teeth 130 cooperate with corresponding ratchet teeth 132 formed on the distal end of housing half sections 12a and 12b. The corresponding ratchet teeth 130 and 132 interact to provide for rotational advancement of collar 128 in a single direction. Also formed on collar 128 are camming surfaces 134 and 136 which interact with camming surfaces 138 and 140 formed at the proximal end of fastener head portion 22. A purpose of collar 128 is to provide for post instrument assembly adjustment of the relative longitudinal positioning of fastener head portion assembly 22 with respect to the distal end of body portion 12. This adjustment capability is important so that instrument 10 can be calibrated to insure the proper positioning of anvil member 24 when cap 51 of anvil approximation indicator member 46 is positioned within opening 54 so as to indicate that instrument 10 is ready for firing of surgical staples 169. Once instrument 10 is properly calibrated, collar member 128 may be fixedly secured to the distal end of body portion 12 so that collar 128 is not permitted to rotate with respect thereto. This attachment may be accomplished by known suitable means such as, for example, bonding and/or by the use of a fastener such as a screw or a pin.

Another important feature illustrated in FIG. 15 provides protection against over crimping of surgical staples 169 upon firing of instrument 10. Pusher back 142 is provided with longitudinally extending portions 144 which are configured to fit inside of knife ring 146 and are preferably sized to abut against a surface portion, such as cut ring 145, of anvil 24 upon firing of instrument 10. When portions 144 of pusher back 142 contact a portion of anvil 24, pusher fingers 52a are prevented from traveling further, thereby limiting the degree to which surgical staples 169 may be crimped against anvil 24.

The basic steps of operation of circular anastomosis devices is known and disclosed. For example, in U.S. Pat. Nos. 4,576,167 issued to Noiles, 5,005,749 issued to Aranyi, and 5,119,983 to Green et al..

With reference to the particular operation of the instrument of the present disclosure, the user positions the tissue to be joined between anvil 24 and fastener head portion 22. Anvil adjustment member 16 is rotated to move elongated member 30 and anvil 24 proximally until the user sees approximation indicator 46 appear in opening 54 of anvil adjustment member 16. During this step, elongate member 30 acts as a tension member as it pulls anvil 24 into position adjacent fastener head portion 22. Prior to alignment of cut out 83 in elongated member 30 and extended portion 79 of lockout 70, lockout 70 is prevented from pivoting by contact between extended portion 79 and elongate member 30. When cut out 83 is positioned adjacent extended portion 79 of lockout 70, as further described below, lockout member 18 and lockout 70 are able to be pivoted by depressing, usually with the thumb, on lockout member 18. Members 18 and 70 can be interconnected by any suitable means, i.e., a protrusion from one member entering a recess in the other.

Once lockout member 18 is pivoted by the user, fastener firing levers 20 are depressed to urge fastener firing member 56 in a distal direction. This distal motion is accomplished by the camming effect of extended portions 60 of fastener firing levers 20 on pusher block 62. The distal movement of fastener firing member 56 urges fastener pusher members to eject fasteners 169 from fastener head portion 22. During this step, fastener firing member 56 acts as a compression member as it ejects fasteners 169.

Referring temporarily to FIGS. 16A–18C, as fastener firing levers 20 are depressed to urge fastener firing member 56 in a distal direction, pusher block 62 moves distally such that extended portion 62a travels distally within longitudinal slot 63a formed centrally through a side of guide 63. As shown in FIGS. 16A and 16B prior to depression or actuation of fastener firing levers 20, bearing block 62 is positioned proximally of pin 267. Upon initial motion of fastener firing levers 20, such as by the user squeezing the handles, pusher block 62 is urged distally, as described above, and travels toward frangible pin 267 as indicated by arrow "A" in FIG. 16B. As the user squeezes fastener firing levers 20 further staples 169 (FIG. 15) are formed completely, and extended portion 62a of pusher block 62 contacts and breaks frangible pin 267 providing both a tactile and audible indication to the user that the staples have been completely formed.

With the above operational description of instrument 10 as a general base of the overall operation, the operation of lockout 70 will now be described in further detail with reference to FIGS. 10–13. Once the user has instrument 10 inserted and the tissue to be joined is properly situated about the distal end of the instrument, anvil 24 is approximated to its proper position by rotation of anvil adjustment member 16, instrument 10 is positioned for firing, as shown in FIG. 10. In that position, however, fastener firing member 56 is still blocked from movement due to lockout member 18 still being oriented in the "safety on" position, i.e., lever locking extended portions 104 and 106 (FIG. 2) are aligned with the structure of levers 20 so that they cannot be depressed.

Pivoting of lockout member 18 is prevented when elongated member 30 is out of the desired approximation range for firing the staples.

With reference to FIGS. 2–7, 11 and 13, prevention of the ability to pivot lockout member 18 is accomplished by the relative position of elongated member 30 and thus the approximation of anvil 24. When anvil 24 is not properly approximated, side wall 80 and web 82 of elongated member 30 prevent extended portion 79 of lockout 70 from moving further inward (FIG. 11). However, once elongated member 30 is properly positioned, i.e., cut out 83 is aligned with extended portion 79 of lockout 70, then lockout member 18 which is fixedly secured to lockout member 70, can be pivoted, as shown in FIG. 13. When lockout 70 is pivoted, shoulder portions 73 and 75 of lockout 70 are moved out of notches 77 of fastener firing member 56 (FIGS. 3 and 4). This enables fastener firing levers 20 to be pivoted toward each other as shown in FIG. 12, thereby moving fastener firing member 56 distally and ejecting fasteners 69 from fastener head portion 22. As can be seen in FIGS. 13 and 13A once lockout member 18, and lockout 70 are pivoted by the user, inwardly extending portion 79 of lockout 70 enters into cut out 83 (FIGS. 6 and 7) and blocks elongated member 30 from movement in either a proximal or distal direction.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical instrument, which comprises:
    a housing having a proximal end portion and a distal end portion;
    an elongated shaft extending from the housing distal end portion, the shaft having a proximal end portion and a distal end portion;
    a tool mechanism operatively positioned at the elongated shaft distal end portion and operable between a first position and a second position;
    an actuation mechanism disposed at least partially within the housing and operatively associated with the tool mechanism, the actuation mechanism being operable between a first position and a second position which defines substantially the full range of movement of the actuation mechanism, to provide corresponding movement of the tool mechanism between the first and second positions, respectively, thereof; and
    an indicator mechanism including a frangible member disposed in the housing and operatively associated with the actuation mechanism, the frangible member providing an audible and tactile indication upon substantially complete movement of the actuation mechanism from the first position to the second position.

2. A surgical instrument according to claim 1, wherein the surgical instrument is adapted to apply at least one staple.

3. A surgical instrument according to claim 1, wherein the frangible member is removably mounted on the housing.

4. A surgical instrument according to claim 1, wherein the frangible member is a pin.

5. A surgical instrument according to claim 1, wherein the frangible member is aluminum.

6. A surgical instrument according to claim 1, wherein the indicator mechanism further includes a guide member having a longitudinal slot formed therein, the frangible member being transversely mounted in the guide member.

7. A surgical instrument according to claim 6, wherein the actuation mechanism includes a block member slidably mounted within the housing, the block member having an extended portion formed thereon configured and dimensioned to slide within the guide member longitudinal slot.

8. A surgical instrument according to claim 7, wherein the frangible member is broken upon distal movement of the block member by a predetermined distance.

9. A surgical instrument according to claim 1, wherein the indicator mechanism is removably mounted on the housing.

10. A surgical instrument for applying at least one circular array of fasteners, comprising:

a housing having a proximal end portion and a distal end portion;

an elongated shaft extending from the housing distal end portion, the shaft having a proximal end portion and a distal end portion;

a fastener carrying cartridge operatively positioned at the elongated shaft distal end portion;

an anvil member operatively disposed adjacent the fastener carrying cartridge;

an actuation mechanism disposed at least partially within the housing and operatively associated with the fastener carrying cartridge to deploy surgical fasteners therefrom;

an indicator mechanism including a frangible member disposed in the housing, spaced from the fastener carrying cartridge and operatively associated with the actuation mechanism, the frangible member positioned to provide an audible and tactile indication upon substantially complete deployment of the surgical fasteners from the fastener carrying cartridge.

11. A surgical instrument according to claim 10, wherein the frangible member is a pin.

12. A surgical instrument according to claim 10, wherein the indicator mechanism further includes a guide member having a longitudinal slot formed therein, the frangible member being transversely mounted in the guide member.

13. A surgical instrument according to claim 12, wherein the actuation mechanism includes a block member slidably mounted within the housing, the block member having an extended portion formed thereon configured and dimensioned to slide within the guide member longitudinal slot.

14. A surgical instrument according to claim 13, wherein the frangible member is broken upon distal movement of the block member a predetermined distance.

15. A surgical instrument according to claim 10, wherein the indicator mechanism is removably mounted on the housing.

16. A circular anastomosis surgical stapling instrument for applying at least one circular array of staples, comprising:

a housing having a proximal end portion and a distal end portion;

an elongated shaft extending from the housing distal end portion, the shaft having a proximal end portion and a distal end portion;

a staple cartridge operatively positioned at the elongated shaft distal end portion;

an anvil member operatively disposed adjacent the staple cartridge;

an actuation mechanism disposed at least partially within the housing and operatively associated with the staple cartridge to eject surgical staples therefrom;

an indicator mechanism including a frangible member disposed in the housing and operatively associated with the actuation mechanism, the frangible member providing audible and tactile indications upon substantially complete ejection of the surgical staples.

17. A surgical instrument according to claim 16, wherein the frangible member is a pin.

18. A surgical instrument according to claim 16, wherein the indicator mechanism further includes a guide member having a longitudinal slot formed therein, the frangible member being transversely mounted in the guide member.

19. A surgical instrument according to claim 18, wherein the actuation mechanism includes a block member slidably mounted within the housing, the block member having an extended portion formed thereon configured and dimensioned to slide within the guide member longitudinal slot.

20. A surgical instrument according to claim 19, the frangible member is broken upon distal movement of the block member by a predetermined distance.

* * * * *